United States Patent
Dolle, III et al.

(10) Patent No.: US 6,175,020 B1
(45) Date of Patent: Jan. 16, 2001

(54) SPIRODIAMINO ACID SCAFFOLD FOR COMBINATORIAL SYNTHESIS

(75) Inventors: Roland Ellwood Dolle, III, King of Prussia, PA (US); Michael C. Barden, Tucson, AZ (US)

(73) Assignee: Pharmacopeia, Inc., Cranbury, NJ (US)

( * ) Notice: Under 35 U.S.C. 154(b), the term of this patent shall be extended for 0 days.

(21) Appl. No.: 09/289,779

(22) Filed: Apr. 9, 1999

Related U.S. Application Data

(60) Provisional application No. 60/081,665, filed on Apr. 14, 1998.

(51) Int. Cl.[7] .................................................. C07D 209/54
(52) U.S. Cl. .................................................. 548/408; 520/1
(58) Field of Search .................................. 548/408; 520/1

(56) References Cited

PUBLICATIONS

Armstrong et al., "Tandem Intramolecular Michael Addition and 1,3–Dipolar Cycloaddition . . . " *J. Chem. Soc., Chem. Comm.* 1327–1328 (1987).

Chiacchio et al. "Stereoselective Synthesis of Isoxazole and Pyrazole Annulated . . . " *Tetrahedron* 53, 13855–13866 (1997).

Gallos et al. "Highly diastereoselective synthesis of densely functionalized . . . " *J. Chem. Soc., Perkin Trans. 1*, 2–4 (1997).

*Primary Examiner*—Joseph K. McKane
*Assistant Examiner*—Taofiq A. Solola
(74) *Attorney, Agent, or Firm*—Heslin & Rothenberg, P.C.

(57) ABSTRACT

Azaspirononanes of formula I and their synthesis

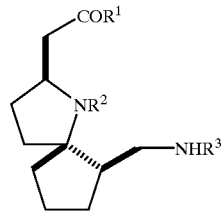

are disclosed. The compounds are useful as templates for constructing synthetic receptors and as intermediates in the synthesis of enzyme inhibitors. They are prepared by an intramolecular ylide cycloaddition of a 6-hydrazone of 2,10-undecadienoic acid ester.

12 Claims, No Drawings

SPIRODIAMINO ACID SCAFFOLD FOR COMBINATORIAL SYNTHESIS

CROSS REFERENCE TO RELATED APPLICATION

This application claims the priority of U.S. application Ser. No. 60/081,665, filed Apr. 14, 1998, the entire disclosure of which is incorporated herein by reference.

FIELD OF THE INVENTION

The invention relates to azaspirononanes, to their synthesis and to their use as templates for the construction of synthetic receptors and libraries thereof and as intermediates in the synthesis of enzyme inhibitors.

BACKGROUND OF THE INVENTION

Receptors are molecules which selectively interact with other molecules. Antibodies, which represent one class of naturally occurring receptor molecules, bind to other molecules (antigens) with very high selectivity; they are also known to catalyze chemical reactions by selectively binding the transition states. Monoclonal antibodies are used as medicinal and diagnostic agents. Although antibodies are proteins, all receptor molecules need not be proteins. Receptor molecules perform a variety of tasks from selective binding of substrates to catalyzing chemical reactions, and their effectiveness is dependent upon their ability to bind molecular species (substrates or acceptors) with high selectivity. For example, the free energy for an antibody binding its antigen is normally from 6–15 kcal/mol.

There is considerable interest in synthetic receptors and libraries thereof For example, Still et al., WO95/19567 have described synthetic receptors which comprise a polyfunctional organic template covalently linked to two or more oligomers. In Still's case, as well as in the present invention, the oligomers may be oligoamides, oligoesters, oligoureas, oligourethanes, oligoamines, oligoethers, oligosulfonamides, oligonucleotides, oligosaccharides, peptides, etc.

In the construction of a library, a template or scaffold (the two will be used interchangeably herein) may be linked to a solid substrate and to an identifier which uniquely defines the synthetic receptor. The identifier is a stable chemical molecule or a plurality of stable chemical molecules distinguishable and detectable to picomolar levels. Usually the template is covalently linked to a solid support which is in turn covalently linked to the identifier, but in some embodiments the template may be directly attached to the identifier. (See PCT application WO 95/19567.)

Throughout this application, various references are referred to within parentheses or square brackets. The disclosures of these publications in their entireties are hereby incorporated by reference into this application. Variables are defined when introduced and retain that definition throughout. The term "combinatorial library" refers to a collection of molecules based on logical design and involving the selective combination of building blocks by means of simultaneous chemical reactions. Each species of molecule in the library is referred to as a member of the library.

SUMMARY OF THE INVENTION

In one aspect, the invention relates to compounds of formula I

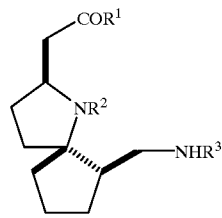

wherein $R^1$ is hydroxy, lower alkoxy, benzyloxy, —$NR^4R^5$ or the residue of a solid substrate; $R^2$ is hydrogen, a first amino-protecting group, or an oligomer residue; $R^3$ is hydrogen, a second amino-protecting group or an oligomer residue; $R^4$ is hydrogen, alkyl, aryl, heterocyclyl, arylalkyl or heterocyclylalkyl; and $R^5$ is hydrogen, alkyl, aryl, heterocyclyl, arylalkyl or heterocyclylalkyl or the residue of a solid substrate. The compounds are useful as scaffolds or templates for constructing synthetic receptors, enzyme inhibitors and libraries of synthetic receptors and enzyme inhibitors.

In another aspect the invention relates to compounds of formula II

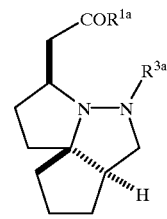

in which $R^{1a}$ and $R^{3a}$ are subsets of $R^1$ and $R^3$. $R^{1a}$ is hydroxy, lower alkoxy or benzyloxy and $R^{3a}$ is hydrogen or an amino-protecting group. These compounds are intermediates in the synthesis of the compounds of formula I.

In another aspect the invention relates to method of preparing a synthetic receptor library, optionally having identifiers associated with members of the library. The library comprises a plurality of different synthetic receptor members. Each synthetic receptor library member will commonly be a solid substrate having a single type of synthetic receptor attached. The method comprises the steps of:

(a) coupling a compound of formula I in which $R^1$ is hydroxy; $R^2$ is a first amino-protecting group, $R^3$ is a second amino-protecting group and $R^2$ and $R^3$ are orthogonally removable, to a solid substrate to provide a substrate-linked template having two protected active sites;

(b) reacting the substrate-linked template with an activator to remove a protecting group therefrom to expose an active site;

(c) coupling a protected oligomer monomer to the exposed active site to provide a protected, nascent oligomer;

(d) reacting the protected, nascent oligomer with an activator to remove a protecting group therefrom to expose an active site; and (e) repeating steps (b) through (d) for each oligomer of the synthetic receptor.

The method may include the additional step of coupling an identifier to the solid substrate between steps (c) and (d).

In another aspect, the invention relates to a process for synthesizing an azaspirononane. The process comprises reacting a compound of formula III

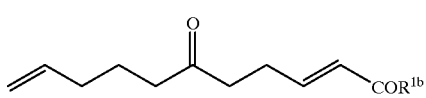

III wherein $R^{1b}$ is lower alkoxy, with a hydrazine of formula $H_2N$—$NH$—$R^{3b}$, wherein $R^{3b}$ is an amino-protecting group, followed by heating to provide a diazatricyclododecane of formula IV

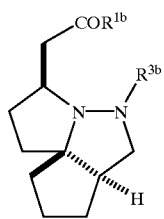

IV

The process may comprise the additional steps of cleaving the amine protecting group $R^{3b}$ and reductively cleaving the N—N bond to provide an azaspirononane of formula V

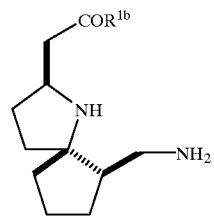

V

The azaspirononane may then be differentially protected as described below.

DETAILED DESCRIPTION OF THE INVENTION

The graphic representations of racemic, ambiscalemic and scalemic or enantiomerically pure compounds used herein are taken from Maehr [*J. Chem. Ed.* 62, 114–120 (1985)]: solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, for example formula I is intended to convey the configurations of the carbons (at 2 and 6) bearing the $CH_2COR^1$ and $CH_2NHR^3$ substituents relative to each other; it does not imply any absolute stereochemistry, i.e. a pure enantiomer having a specified configuration at the 2 and 6 positions of the azaspirononane. The use of Maehr's convention avoids the misleading suggestion of absolute stereochemistry that is unfortunately conveyed by the more common graphic representations found in the literature. The scaffolds of the present invention can certainly be prepared and used as individual enantiomers, as discussed below, but that is not necessary to the practice of the invention.

The invention relates to compounds of formula I

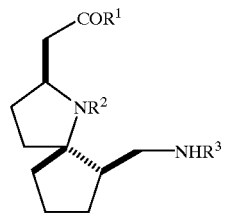

I wherein $R^1$ is hydroxy, lower alkoxy, benzyloxy or the residue of a solid substrate; $R^2$ is hydrogen, a first amino-protecting group, or an oligomer residue; and $R^3$ is hydrogen, a second amino-protecting group or an oligomer residue. A preferred subset of the genus includes (A) those subgenera in which $R^1$ is hydroxy and particularly (Aa) those in which $R^2$ is a first amino-protecting group and $R^3$ is a second amino-protecting group and (Ab) those in which one of $R^2$ and $R^3$ is hydrogen and the other is chosen from t-butoxycarbonyl, allyloxycarbonyl, benzyloxycarbonyl, and fluorenylmethoxycarbonyl. The carboxylic acid and the amines are protected with any of the well-known protecting groups for acids and amines. [See Greene and Wuts *Protective Groups in Organic Synthesis* Second Edition John Wiley & Sons, New York 1991, pages 224–276 and 309–370 which are incorporated herein by reference.]. The term "amino-protecting group" refers to the groups described by Greene and Wuts for amines and to similar groups for the same purpose. Preferred protecting groups are lower alkyl esters for the acid and orthogonal urethanes for the amine. Methods for protecting and deprotecting with these groups are found in Greene and Wuts on pages 227–231, and 315–349 respectively. Orthogonal protecting groups are groups that can be selectively removed in the presence of each other. For example t-Boc is orthogonal to allyloxy in that t-Boc is cleaved by anhydrous acid, while allyloxy is stable to anhydrous acid; conversely allyloxy is cleaved by Pd(0) species in the presence of a reducing agent, while t-Boc is stable. Preferred embodiments of subgenus (Aa) are those in which one of $R^2$ and $R^3$ is t-butoxycarbonyl and the other is chosen from allyloxycarbonyl, benzyloxycarbonyl, and fluorenylmethoxycarbonyl. This subgenus is useful for attaching to a solid substrate as a scaffold for preparing libraries of receptors.

Another preferred subset of the genus includes (B) those subgenera in which $R^1$ is the residue of a solid substrate and particularly (Ba) those in which $R^2$ and $R^3$ are oligomer residues and (Bb) those in which $R^2$ is a first amino-protecting group and $R^3$ is a second amino-protecting group. Subgenus (Ba) includes synthetic receptors and precursors thereto; subgenus (Bb) includes intermediates for libraries. The preferred protecting groups are as before.

A third preferred subset of the genus includes (C) those subgenera in which $R^1$ is lower alkyl, one of $R^2$ and $R^3$ is hydrogen and the other is chosen from t-butoxycarbonyl, allyloxycarbonyl, benzyloxycarbonyl, and fluorenylmethoxycarbonyl. Subgenus (C) represents primarily synthetic intermediates in the synthesis of the scaffolds.

Other synthetic intermediates in the synthesis of the scaffolds are compounds of formula II

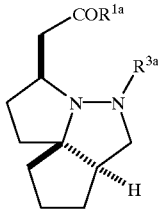

II in which $R^{1a}$ is hydroxy, lower alkoxy or benzyloxy and $R^{3a}$ is hydrogen or an amino-protecting group. Preferred subgenera include (A) those in which $R^{1a}$ is hydroxy and $R^{3a}$ is chosen from t-butoxycarbonyl, allyloxycarbonyl, benzyloxycarbonyl, and fluorenylmethoxycarbonyl, preferably t-butoxycarbonyl; and (B) those in which $R^{1a}$ is lower alkoxy and $R^{3a}$ is chosen from t-butoxycarbonyl, allyloxycarbonyl, benzyloxycarbonyl, and fluorenylmethoxycarbonyl. A preferred subgenus (B) is that in which $R^{1a}$ is methoxy or ethoxy and $R^{3a}$ is t-butoxycarbonyl.

The compounds of the invention are prepared by reacting a compound of formula III

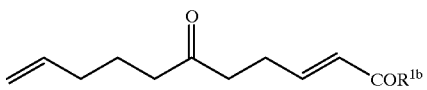

III wherein $R^{1b}$ is lower alkoxy, with a hydrazine of formula $H_2N-NH-R^{3b}$, wherein $R^{3b}$ is an amino-protecting group, in an inert solvent at >100° C. to provide a diazatricyclododecane of formula IV

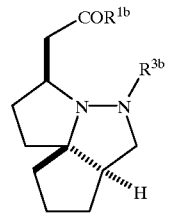

IV

The amine protecting group $R^{3b}$ is then cleaved and the N—N bond is cleaved to provide an azaspirononane of formula V

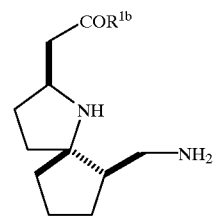

V

The nitrogens of the azaspirononane may then be differentially protected and the ester cleaved.

The starting vinyl ketoester III is available by the method of Armstrong [*J. Chem. Soc., Chem. Com.* 1987, 1327–1328]. Various $R^{1b}$ groups can be obtained by substituting the appropriate ester for Armstrong's Wittig reagent. When $R^{1b}$ is methoxy or ethoxy, it can be conveniently cleaved by alkali metal hydroxide in an aqueous solvent; when $R^{1b}$ is t-butoxy, it can be cleaved by acid; when $R^{1b}$ is benzyloxy, it can be cleaved by hydrogenolysis. The necessary hydrazines and hydrazides are commercially available or are synthesized by methods well-known in the art. When $R^{3b}$ is benzyl, the cleavage of the protecting group and the cleavage of the N—N bond may be accomplished in one step. Cleavage of the N—N bond is usually accomplished by catalytic hydrogenation in the presence of a noble metal catalyst. A prototypical synthesis is shown in Scheme 1. In this scheme $R^{1b}$ is ethoxy, $R^{3b}$ is t-butoxycarbonyl and the product V is further protected at $R^2$ with allyloxycarbonyl before saponification of the ester:

Scheme 1

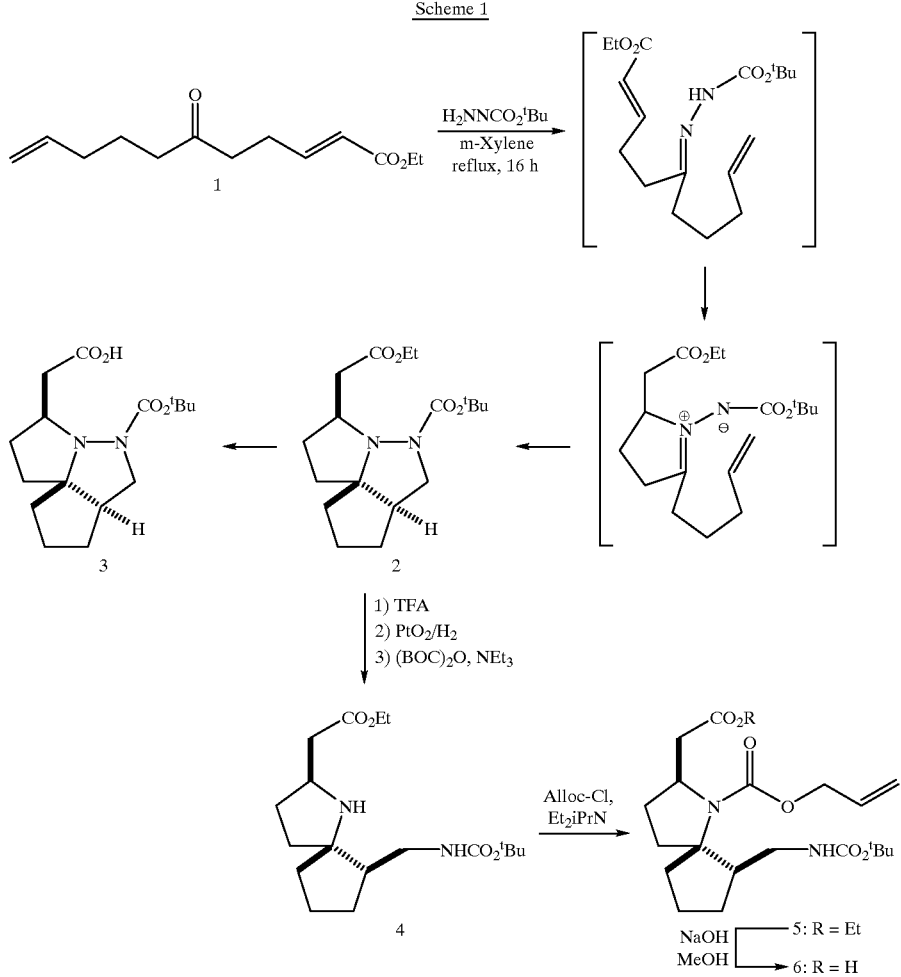

Individual enantiomers, if desired, can be obtained by conventional resolution of 4 with an optically pure acid or by resolution of 6 with an optically pure amine.

According to Still et al., templates for synthetic receptors desirably have limited conformational mobility and have their functionality oriented in such a way that the receptor "arms", usually variable oligomeric chains, are directed toward nearby regions of space. The spirodiarinoacid I of the invention is thus well suited as a template.

One class of synthetic receptors based on the spirodiaminoacid I of the invention may have the following general formula:

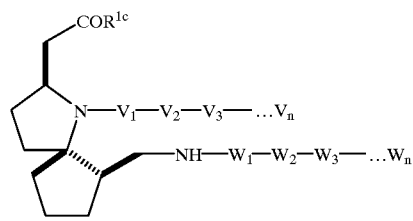

wherein $R^{1c}$ is hydroxy, lower alkoxy, benzyloxy or $NHR^4$. V is an oligomer monomer and W is an oligomer monomer. $V_1$ to $V_n$ and $W_1$ to $W_n$ are the oligomer arms. The individual monomers may be the same or different, as will be understood from PCT application WO 95/19567. A synthetic receptor library will consist of a collection of such synthetic receptor molecules (i.e. a library) having a variety of different oligomers. The spirodiamino acid scaffold is attached to a solid support particle as diagramed below such that any given solid support particle has only one type of synthetic receptor (i.e. one type of synthetic receptor member of the library) bound to it.

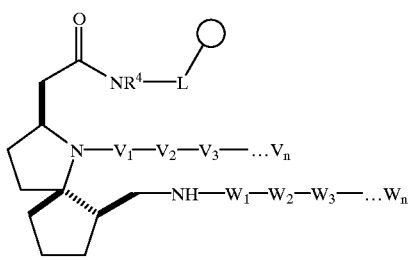

In this depiction,

represents a solid support and L represents a linker.

The synthetic receptors may (a) bind an acceptor molecule; (b) exhibit biological activity; (c) catalyze a reaction; (d) inhibit a catalyzed reaction; or (e) function as a stationary phase in chromatography.

A substrate of interest, detectable at nanomolar levels by way of its color, its fluorescence, its radioactivity, etc., may be prepared. Such detectable substrates are referred to herein as labeled substrates. The synthetic receptor library is then assayed to find those members of the library which have the desired interaction with the labeled substrate. In the case where the desired interaction is binding to the substrate, the synthetic receptor library is mixed with a solution of the labeled substrate and those library members that bind to the labeled substrate are selected. This procedure is particularly simple when the synthetic receptor library members are bound to a solid support as shown in Scheme 3. Solid support particles having receptors which bind the labeled substrate accumulate color or fluorescence or radioactivity (depending on the nature of the label used). Depending on the concentration of the labeled substrate used, the assay can be adjusted to detect binding of any desired strength: for example, if the amount of labeled substrate in the presence of the receptor library is adjusted to give a 100 $\mu$M concentration of free (unbound) labeled substrate, then assay will only detect template-substrate binding with association constants (k) of $(100\ \mu M)^{-1}$ or greater. Libraries of synthetic receptors may be similarly assayed for synthetic receptor(s) that catalyze a reaction or inhibit an enzyme-catalyzed reaction. The receptor libraries can also be used to find receptors to detect a drug, for example, an illicit drug.

Although their primary use is envisioned in the creation of libraries of test compounds or receptors on solid supports, synthetic receptors incorporating the scaffold of the invention can also be used in affinity chromatography [Eveleigh, J. W. & Levy, D. E. Immunochemical characteristics and preparative application of agarose-based immunosorbents, *J. Solid Biochem.* 2, 45–78 (1977)]. Any gel may be used that offers the possibility of attaching the carboxylic acid residue. Thus gels that have amine and hydroxyl functionalities are particularly suitable. The scaffold is attached by methods well known in the art for preparing affinity gels.

A library is synthesized using combinatorial techniques. The library may be prepared by any of the known methods for combinatorial synthesis [G. Jung and A. G. Beck-Sickinger, *Angew. Chem. Int. Ed.* 31, 367–383 (1992); Pavia et al., *Bioorg. Med. Chem. Lett.* 3, 387–396 (1993)]. Combinatorial synthetic techniques include the multi-pin method [Geysen et. al., *Proc. Natl. Acad. Sci. USA* 81, 3998 (1984); Geysen et al., *Proc. Natl. Acad. Sci. U.S.A.* 82 178 (1985); WO 84/03564; WO 86/06487; WO 86/00991; and U.S. Pat. No. 5,133,866], the tea-bag method [U.S. Pat. No. 4,631,211; Houghton et al., Int. *J. Peptide Protein Res.* 27, 673 (1986); Houghton et al., *Biotechniques* 4 522–528 (1986); Houghten, *Proc. Natl. Acad. Sci. USA* 82, 5131 (1985); WO 92/09300], the cellulose-paper method [Frank and Doering *Tetrahedron Lett.* 44, 6031 (1988)], the light-directed method (also termed as VLSIPS method,) [Fodor et. al., *Science* 251, 767 (1991); U.S. Pat. No. 5,143,854; WO 90/15070; WO 92/10092] and the split-synthesis method [Lam et al. *Nature* 354; 82 (1991); WO 92/00091, WO 93/06121]. The procedure for split synthesis involves creating a large library consisting of thousands to billions of different test compounds attached to particles such as beads, with each bead containing a single oligomer sequence and with the collection representing numerous combinations of possible random oligomer sequences.

The "one-bead, one-oligomer sequence" concept can be achieved easily by separating and mixing beads during the synthesis. For structure elucidation, readable tags (oligonucleotide tag or peptide tag) are cosynthesized to encode the series of steps and reagents used in the synthesis of each library element [Brenner and Lerner, *Proc. Natl. Acad. Sci USA* 89, 5381 (1992); Kerr et. al., *J Am. Chem. Soc.* 115, 2529 (1993)]. Once a library element is selected by certain assay, its structure can be identified by its tag. The preferred encoding method is that of Ohlmeyer et al., as described in [*Proc. Nati. Acad. Sci. USA*, 90, 10922–10926 (1993); and PCT application WO 94/08051]. This technique makes use of highly sensitive, chemically inert molecular tags and a binary encoding scheme to provide a practical solution for the construction of large, chemically diverse libraries.

The materials upon which combinatorial syntheses are performed are referred to as solid supports, beads, and resins. These terms include: (a) beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have surfaces that have been functionalized with amino, hydroxy, carboxy, or halo groups; amino groups are most common. Techniques for functionalizing the surface of solid phases are well known in the art. Attachment of lysine to the surface of a bead (to increase the number of available sites) and subsequent attachment of linkers as well as further steps in a typical combinatorial synthesis are described, for example, in PCT application WO95/30642, the disclosure of which is incorporated herein by reference.

Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. A number of linkers have been described in the literature [Backes et al., *Current Opinion in Chemical Biology* 1, 86–93 (1997)]. When used below and in the claims, the term "solid substrate" or "residue of a solid substrate" includes both the base resin, bead etc (usually referred to as the solid support) and the linker. The preparation of a solid substrate is shown in Scheme 2. Because of the particular linker, L, chosen (5) in Scheme 2, the scaffolds can be cleaved from the solid phase with actinic radiation.

Scheme 2.

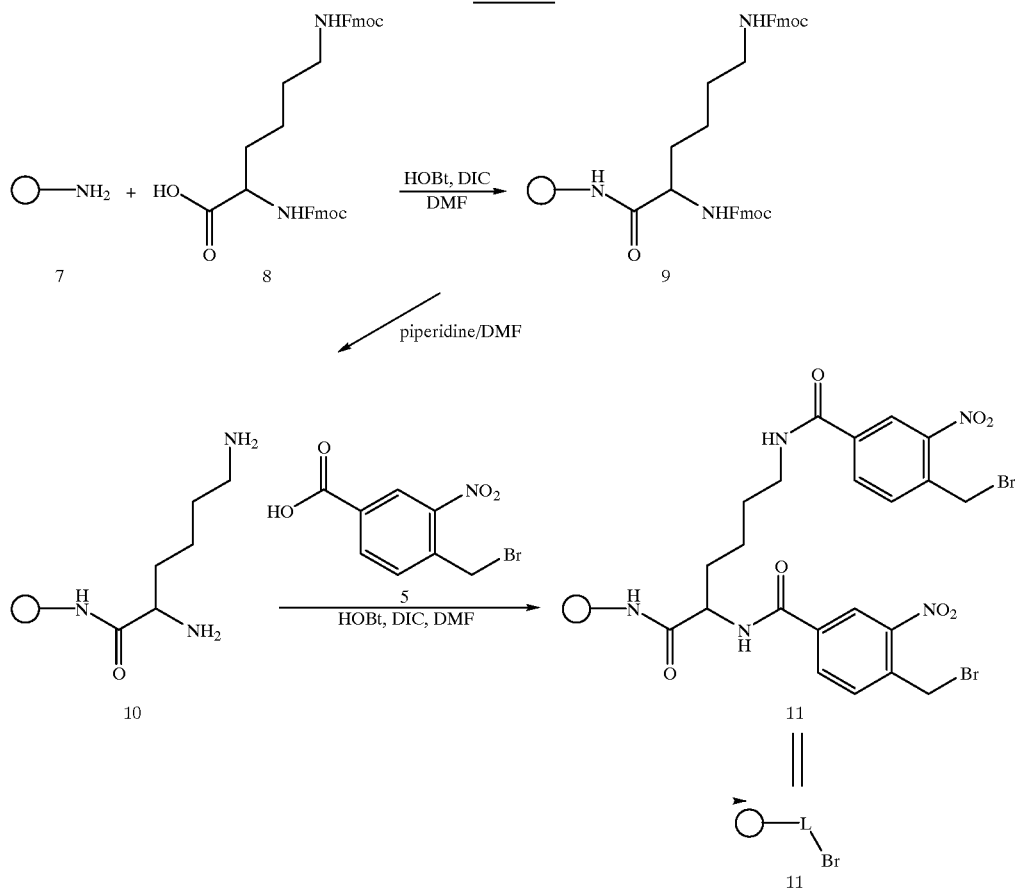

In the particular examples shown in Schemes 3 and 4, the template is attached via a photolabile linker to a resin through an intervening amine ($R^1$ is $NR^4R^5$, $R^4$ is arylalkyl and $R^5$ is the residue of a solid substrate), and the amine residue remains a part of the receptor when it is cleaved from the solid substrate. In the case in which the template would be attached via a linker, L, to a resin without an intervening amine (i.e., $R^1$ is a solid substrate), a support having the 4-[4-(hydroxymethyl)-3-methoxyphenoxy]butyryl residue as a linker can be employed. This linker is attached to a resin having amino functionalities by forming an amide with the carboxyl of the butyric acid chain. The N-protected scaffold is attached to the hydroxyl of the 4-hydroxymethyl group via its carboxyl to form a 2,4-dialkoxybenzyl ester, which can be readily cleaved in acid media when the synthesis is complete [see for example Riniker et al. *Tetrahedron* 49 9307–9312 (1993)].

Libraries containing the scaffold of the invention, but having small molecules rather than oligomers attached, are also of interest for developing drugs, for example antimalarial drugs. Resistance to known antimalarial therapies is becoming an increasing problem, and new therapies are therefore desperately needed. Upon infecting a host, the malaria parasite avidly consumes the host hemoglobin as its source of nutrients. Plasmepsin I and II are proteases from *Plasmodium falciparum* that are necessary during the initial stages of hemoglobin hydrolysis and digestion. It has been shown that inhibition of plasmepsin by a peptidomimetic inhibitor is effective in preventing malarial hemoglobin degradation and in killing the parasite. Thus, persons of skill in the art expect that plasmepsin inhibitors will provide effective antimalarial therapy. The synthesis of prototypical members of such a library are shown in Schemes 3 and 4. Compound 23 (Scheme 4) is a plasmepsin inhibitor having an $IC_{50}$ below 1 millimolar in the assay described below.

Scheme 3
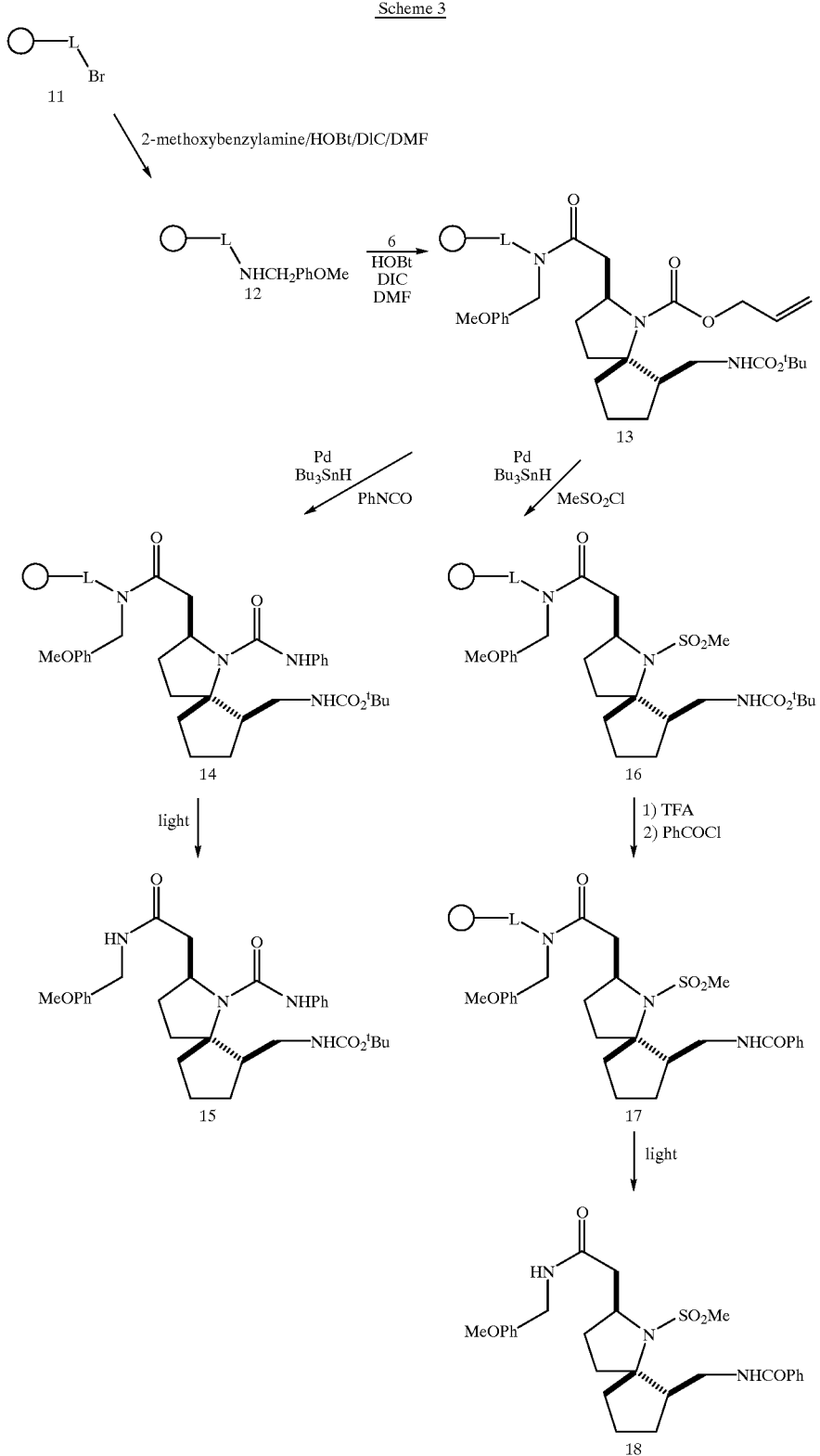

Scheme 4

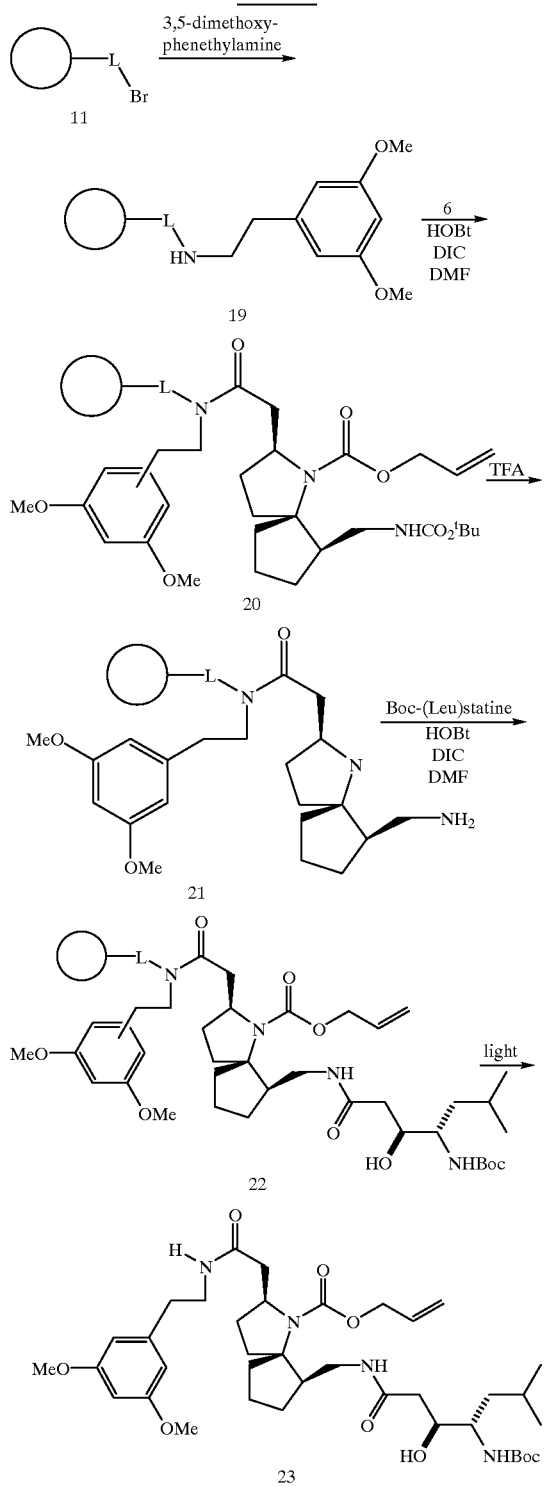

Abbreviations and Definitions

The following abbreviations and terms have the indicated meanings when they occur; all of the abbreviations do not necessarily occur in the application:

| | |
|---|---|
| Ac | = acetyl |
| BNB | = 4-bromomethyl-3-nitrobenzoic acid |
| Boc | = t-butyloxy carbonyl |
| Bu | = butyl |
| c- | = cyclo |
| DCM | = dichloromethane = methylene chloride = $CH_2Cl_2$ |
| DIC | = diisopropylcarbodiimide |
| DIEA | = N,N-diisopropylethyl amine |
| DMAP | = 4-N,N-dimethylaminopyridine |
| DMF | = N,N-dimethylformamide |
| DMSO | = dimethyl sulfoxide |
| Fmoc | = 9-fluorenylmethoxycarbonyl |
| GC | = gas chromatography |
| HOAc | = acetic acid |
| HOBt | = hydroxybenzotriazole |
| Me | = methyl |
| mesyl | = methanesulfonyl |
| PEG | = polyethylene glycol |
| Ph | = phenyl |
| rt | = room temperature |
| sat'd | = saturated |
| s- | = secondary |
| t- | = tertiary |
| TFA | = trifluoroacetic acid |
| THF | = tetrahydrofuran |

Alkyl is intended to include linear, branched, or cyclic hydrocarbon structures and combinations thereof. Lower alkyl refers to alkyl groups of from 1 to 4 carbon atoms. Examples of lower alkyl groups include methyl, ethyl, propyl, isopropyl, butyl, s-and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S; each of which rings is optionally substituted with 1–3 lower alkyl, substituted alkyl, halogen or alkoxy.

The aromatic 6- to 14-membered carbocyclic rings include, e.g., benzene, naphthalene, indane, tetralin, and fluorene and the 5- to 10-membered aromatic heterocyclic rings include, e.g., iridazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Heterocyclylalkyl means an alkyl residue attached to a heterocycle. Examples include, e.g., pyridinylmethyl, morpholinoethyl and the like.

Heterocycle means a cycloalkyl or aryl residue in which one to two of the carbons is replaced by a heteroatom such as oxygen, nitrogen or sulfuir. The term heterocycle includes heteroaryl as described above. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Synthesis of Azaspirononane 6 as Shown in Scheme 1:

Ethyl ester 1 (15 g, 71.5 mmol) and t-butylcarbazate (12.2 g, 92.5 mmol) were dissolved in diethyl ether (240 mL) and the reaction mixture was stirred for 3 days (Scheme 1). The resulting heterogeneous mixture was concentrated in vacuo followed by the addition of 500 mL of m-xylenes. The mixture was refluxed overnight. After cooling, the solution was concentrated and the residue was purified by silica gel chromatography to afford the tricyclic product 2 (11.10 g. 49% yield) as a pale yellow oil. $^1$H-NMR (CDCl$_3$): δ 3.72 (m, 1H), 3.64 (s, 3H), 3.45 (m, 1H), 3.11 (m, 1H), 2.88 (m, 1H), 2.34 (m, 2H), 1.88 (m, 6H), 1.56 (m. 4H). 1.42 (s 9H). $^{13}$C-NMR (CDCl$_3$): δ 172.96, 81.64, 79.73, 63.39, 51.64, 51.26, 41.03, 39.48, 35.87, 32.38, 29.73, 28.19, 25.51.

An alternative process for 2:

A solution of ketone 1 (methyl ester, 0.637 g, 3.03 mmol) and t-butylcarbazate (0.437 g, 3.31 mmol) was stirred in diethyl ether (10 mL) at room temperature overnight. The resulting mixture was filtered and the white precipitate was washed with several portions of cold hexanes. The residual solvent was removed in vacuo to give 0.95 g (97% yield) of the corresponding hydrazone as colorless solid: R$_f$=0.45 (30% EtOAc in hexanes); mp=103–105° C.; IR (thin film on NaCl) 3278, 2976, 1739, 1695 cm$^{-1}$; $^1$H NMR (CDCl$_3$) δ 7.53 (broad s, 1), 6.98 (dt, 1, J=6.6, 15.9), 5.86 (dt, 1, J=1.5, 15.6), 5.78 (m, 1), 5.07 (m, 2), 3.72 (s, 3), 2.51 (m, 4), 1.60 (quartet, 2, J=7.6), 1.51 (s, 9); $^{13}$C NMR (CDCl$_3$) δ 166.86, 148.29, 137.22, 121.33, 116.16, 80.89, 51.41, 51.24, 34.94, 33.18, 28.66, 28.25, 28.07, 27.98, 24.08; MS (ES+) m/z 225 [(M-Boc)H]$^+$, 269 [(M-t-Bu)H]$^+$, 325 (MH)$^+$; HRMS (FAB) calcd for C$_{17}$H$_{28}$N$_2$O$_4$ 325.2127, found 325.2134.

The hydrazone (0.454 g, 1.40 mmol) was dissolved in 136 mL of anhydrous, denatured ethanol and heated at reflux for 72 h. The solution was concentrated to a clear oil which was purified by flash chromatography (20% EtOAc in hexanes; R$_f$=0.25) to afford 0.343 g (76%) of 2 as a clear oil: IR (thin film on NaCl) 3444, 2952, 2868, 1738, 1692 cm$^{-1}$; $^1$H NMR (DMSO-d6) δ 3.64 (d, 1, J=9.6), 3.56 (s, 3), 3.33 (broad s, 1), 3.04 (septet, 1, J=4.7), 2.67 (dd, 1, J=4.8, 15.9), 2.33 (dd, 1, J=8.4, 15.6), 2.33, (m, 1), 1.95–1.77 (m, 4), 1.68 (dt, 1, J=6.3, 7.8), 1.59 (dt, 1, J=6.3, 7.8), 1.49–1.40 (m, 3), 1.38 (s, 9), 1.27 (m, 1); MS (ES+) m/z 225 [(M-Boc)H]$^+$, 269 [(M-t-Bu)H]$^+$, 325 (MH)$^+$; HRMS (FAB) calcd for C$_{17}$H$_{28}$N$_2$O$_4$ 325.2127, found 325.2136.

Cycloadduct 2 was fuirther characterized as its carboxylic acid 3. Cycloadduct 2 (0.23 g, 0.72 mmol) was dissolved in 1 N KOH in methanol (10 mL) and the reaction mixture was stirred overnight. The solvent was removed under reduced pressure. The residue was taken up in a solution of saturated aqueous NAHCO$_3$, and was washed with EtOAc to remove organic impurities. The solution was acidified with citric acid to pH~2–3 and was extracted with ethyl acetate. The ethyl acetate extracts were combined, dried (Na$_2$SO$_4$), and the solvent removed under reduced pressure. Purification by column chromatography eluting with 1:1 hexanes:ethyl acetate gave 0.17 g of a colorless solid (76% yield). Re-crystallization of the acid 3 from acetone gave analytically pure material. $^1$H-NMR (CDCl$_3$): δ 3.84 (m, 1H), 3.40 (m, 1H), 3.10 (m, 1H), 2.81 (d, 1H), 2.42 (m, 2H), 1.97 (m, 6H), 1.56 (m, 4H), 1.48 (s, 9H). $^{13}$C-NMR (CDCl$_3$): δ 172.25, 82.01, 63.48, 51.57, 50.29, 41.18, 38.00, 35.75, 31.82, 28.47, 28.06, 25.52. Mass spectrum (m/z): 311.21, 307.11, 289.09, 255.14, 254.13, 210.14.

Cycloadduct 2 (11.10 g, 34.21 mmol) was dissolved in 25% trifluoroacetic acid/CH$_2$Cl$_2$ and the reaction mixture was stirred for 1 hr. The solvent and excess acid were removed under reduced pressure to give a dark brown oil. The oil was taken up in 1M HCl/MeOH (100 mL) to which was added PtO$_2$ (1.0 g, 4.41 mmol). The heterogeneous reaction mixture was pressurized to 80 psi under an atmosphere of hydrogen gas and the reaction mixture was shaken overnight. The mixture was filtered and the solvent removed under reduced pressure to give a tan colored oil. This oil was dissolved in 250 mL of CH$_2$Cl$_2$ containing Et$_3$N (9.50 mL, 68.16 mmol) and (BOC)$_2$O (11.20 g, 51.32 mmol). The solution was stirred at room temperature overnight. The solvent was removed under reduced pressure and the product was purified by column chromatography eluting with 1:1 hexanes: ethyl acetate to remove excess BOC reagent, then with (10:1:0.1) CH$_2$Cl$_2$:MeOH:NH$_4$OH to recover 9.8 g of 4 as a colorless oil (87% yield). Mass spectrum (m/z): 341 (M+H).

A solution of 4 (12.8 g, 39.18 mmol) in CH$_2$Cl$_2$ (200 mL) was treated with DIEA (20.60 mL, 118.26 mmol) and allyl chloroformate (8.30 mL, 78.22 mmol). The reaction mixture was stirred overnight. The solvent was removed under reduced pressure and the residue was treated with 0.5M aqueous citric acid for 15 min, then was extracted with 3×50 mL CH$_2$Cl$_2$. The extracts were combined, dried (Na$_2$SO$_4$), and the solvent was removed under reduced pressure. The product was purified by column chromatography eluting with (4:1) hexanes:ethyl acetate to give 12.5 g of 5 as a colorless oil (77 % yield). Mass spectrum (m/e) 425 (M+H).

A solution of 5 (12.5 g, 30.40 mmol) in 1N NaOH/MeOH (50 mL) was stirred at room temperature for 5 h. The solvent was removed under reduced pressure and the residue was taken up in saturated aqueous Na$_2$HCO$_3$ (100 mL) and washed with 2×20 mL CH$_2$Cl$_2$ to remove organic impurities. The aqueous layer was acidified to pH~3 with aqueous citric acid and extracted with 3×50 mL EtOAc. The combined organic extracts were dried (Na$_2$SO$_4$), and the solvent removed to give a yellow oil. The product was purified by column chromatography eluting with (1:1) hexanes: ethyl acetate to give a solid residue which was then re-crystallized from hexanes/ethyl acetate to give 9.6 g of the crystalline solid acid 6 (80% yield). $^1$H-NMR (CDCl$_3$): δ 5.93 (m, 1H), 5.26 (m, 2H), 4.76 (broad s, 1H), 4.55 (m, 2H), 4.33 (broad s, 1H), 3.33 (broad s, 1H), 3.08 (m, 1H), 2.92 (m, 2H), 2.33 (m, 1H), 2.13 (m, 1H), 1.89 (m, 6H), 1.70 (m, 2H), 1.43 (s, 9H). $^{13}$C-NMR (CDCl$_3$): δ 176.06, 154.37, 132.83, 117.35, 79.13, 72.27, 65.39, 56.01, 50.79, 42.55, 42.08, 38.74, 37.65, 31.27, 28.24, 27.53, 24.08. Mass spectrum (m/z): 397 (M+H).

Synthesis of Resin 11 as Shown in Scheme 2:

TENTAGEL™ resin 7 (1.2 g, 0.32 mmol/g, 0.384 mmol, 180–220 μm, Scheme 2) was suspended in a solution of bis-Fmoc lysine 8 (1.12 mmol, 0.68 g), and HOBt (1.12 mmol, 0.15 g), then treated with DIC (2.2 mmol, 0.36 mL). The suspension was shaken overnight, then drained and washed with DMF (3×15 mL), MeOH (3×15 mL) and DCM (3×15 mL) to furnish resin 9.

A suspension of the Fmoc resin 9 (1.2 g) in 1:1 piperidine-DMF was shaken for 1.5 hours, then drained and washed with DMF (3×15 mL), MeOH (3×15 mL) and DCM (3×15 mL). Resin 10 so obtained was suspended in DMF (4 mL) and treated with a pre-incubated (one hour) solution of 4-bromomethyl-3-nitro benzoic acid (2.2 mmol, 0.58 g), HOBt (2.3 mmol, 0.3 g), DIC (4.5 mmol, 1 mL) in DMF (6 mL). The suspension was shaken overnight, then drained and washed with DMF (3×15 mL), methanol (3×15 mL) and DCM (3×15 mL) to furnish resin 11.

Attachment of Scaffold Azaspirononane 6 to Resin and Synthesis of Models for Receptors, as Shown in Scheme 3:

The suspension of the resin 11 (1 g) in THF (10 mL) was treated with 2-methoxy benzyl amine (3 mmol) and was shaken overnight. The resin was then drained and washed with DMF (3×5 mL), MeOH (3×15 mL), and DCM (3×15 mL). The resin 12 was filtered and dried overnight in vacuo.

Resin 12 so obtained was suspended in DMF (5 mL) and treated with acid 6 (2.2 mmol, 0.58 g), HOBt (2.3 mmol, 0.3 g), DIC (4.5 mmol, 1 mL) in DMF (6 mL). The suspension was shaken overnight, then drained and washed with DMF (3×15 mL), methanol (3×15 mL) and DCM (3×15 mL) to furnish resin 13.

A suspension of resin 13 (0.5 g) in CH$_2$Cl$_2$ (10 mL) was treated with HOAc (4.8 mmol, 0.27 mL), Pd(PPh$_3$)$_4$ (0.072 mmol, 83 mg), then Bu$_3$SnH (2.4 mmol, 0.64 mL). The suspension was shaken for 1 hr, then drained and washed with CH$_2$Cl$_2$ (3×10 mL), pyridine (3×10 mL), CH$_2$Cl$_2$ (3×10 mL), then DMF (3×10 mL). The resin was re-suspended in acetonitrile (10 mL) and was then treated with phenyl isocyanate (0.72 mmol, 0.13 mL). The suspension was shaken 12 h, then drained and washed with CH$_2$Cl$_2$ (3×10 mL), DMF (3×10 mL), MeOH (3×10 mL), DMF (3×10 mL), and CH$_2$Cl$_2$ (3×10 mL). The resin 14 was dried in vacuo.

Resin 14 was suspended in MeOH (20 mL) and the compound cleaved from the resin by heating the suspension to 50° C. and irradiating for 3–4 hr at 353 nm. The suspension was filtered and the MeOH removed to give the title compound 15 as confirmed by mass spectroscopy: Mass spectrum: m/z=551 (M+H$^-$).

A suspension of resin 13 (0.5 g) in CH$_2$C2 (10 mL) was treated with HOAc (4.8 mmol, 0.27 mL), Pd(PPh$_3$)$_4$ (0.072 mmol, 83 mg), then Bu$_3$SnH (2.4 mmol, 0.64 mL). The suspension was shaken for 1 hr, then drained and washed with CH$_2$Cl$_2$ (3×10 mL), pyridine (3×10 mL), CH$_2$Cl$_2$ (3×10 mL), then DMF (3×10 mL). The resin was resuspended in pyridine (10 mL) and was then treated with methylsulfonyl chloride (1.1 mmol). The suspension was shaken 12 h, then drained and washed with CH$_2$Cl$_2$ (3×10 mL), DMF (3×10 mL), MeOH (3×10 mL), DMF (3×10 mL), and CH$_2$Cl$_2$ (3×10 mL). The resin 16 was dried in vacuo.

Resin 16 was suspended in 25% trifluoroacetic acid in DCM (5 mL). The suspension was shaken overnight, then drained and washed with DCM (3×15 mL), methanol (3×15 mL) and DCM (3×15 mL). The resin so obtained was re-suspended in pyridine (10 mL) to which was added benzoyl chloride (2 mmol). The suspension was shaken for 6 hours and then washed with CH$_2$Cl$_2$ (3×10 mL), DMF (3×10 mL), MeOH (3×10 mL), DMF (3×10 mL), and CH$_2$Cl$_2$ (3×10 mL). The resin 17 was dried in vacuo.

Resin 17 was suspended in MeOH (20 mL) and the compound cleaved from the resin by heating the suspension to 50° C. and irradiating for 3–4 hr at 353 nm. The suspension was filtered and the MeOH removed to give the title compound 18 as confirmed by mass spectroscopy: Mass spectrum: m/z=514 (M+H$^-$).

Attachment of Scaffold Azaspirononane 6 to Resin and Synthesis of a Member of a Plasmepsin Inhibitor Library, as Shown in Scheme 4:

The suspension of the resin 11 (1 g) in THF (10 mL) was treated with 3,5-dimethoxyphenethylamine (3 mmol) and was shaken overnight. The resin was then drained and washed with DMF (3×15 mL), MeOH (3×15 mL), and DCM (3×15 mL). The resin 12 was filtered and dried overnight in vacuo. Resin 19 so obtained was suspended in DMF (5 mL) and treated with acid 6 (2.2 mmol, 0.58 g), HOBt (2.3 mmol, 0.3 g), DIC (4.5 mmol, 1 mL) in DMF (6 mL). The suspension was shaken overnight, then drained and washed with DMF (3×15 mL), methanol (3×15 mL) and DCM (3×15 mL) to furnish resin 20.

Resin 20 was suspended in 25% trifluoroacetic acid in DCM (5 mL). The suspension was shaken overnight, then drained and washed with DCM (3×5 mL), methanol (3×15 mL) and DCM (3×15 mL) to give resin 21.

Resin 21 was suspended in DMF (10 mL) to which was added was suspended in a solution of Boc-(Leu)statine (1.12 mmol, 0.68 g), and HOBt (1.12 mmol, 0.15 g), then treated with DIC (2.2 mmol, 0.36 mL). The suspension was shaken overnight, then drained and washed with DMF (3×15 mL), MeOH (3×15 mL) and DCM (3×5 mL) to furnish resin 9.

Resin 14 was suspended in MeOH (20 mL) and the compound cleaved from the resin by heating the suspension to 50° C. and irradiating for 3–4 hr at 353 nm. The suspension was filtered and the MeOH removed to give the title compound 15 as confirmed by proton NMR: (CDCl$_3$ δ) 6.15s, 5.90s, 5.51–5.40 m, 3.90–4.80 m, 3.8s, 3.70 m, 2.60–2.95 m, 1.20–2.40 m, 0.09d.

Biological Assay for Plasmepsin II

The assay mix contained 50 mM sodium acetate (pH 5.0), 1 mg/ml BSA, 0.01% Tween 20, 12.5% glycerol, 18% DMSO and 12 μM plasmepsin substrate. Twenty five μL of the assay mix is added to each well of the 96-well microtiter plate containing dried down bead eluate or empty control wells. The plates are then sonicated and mixed. Then 25 μL of 8 nM plasmepsin II which is in 50 mM sodium acetate (pH 5.0), 1 mg/ml BSA, 0.01% Tween 20, and 12.5% glycerol, is added to the assay mix. The final concentrations are 4 nM plasmepsin II, 6 μM plasmepsin substrate, 9% DMSO, 50 mM sodium acetate (pH 5.0), 1 mg/ml BSA, 0.01% Tween 20, and 12.5% glycerol. The reaction is incubated for 10 minutes at 25° C. and then quenched by the addition of 25 μL of 1 M Tris (pH 8.5) and 50% DMSO to achieve a final concentration of 0.33 M Tris and 23% DMSO. The EDANS fluorescence was measured using the Tecan, SLT FLUOSTAR® fluorescence plate reader with an excitation filter of 350 nm and and an emission filter 510 nm. The background was determined by 25 μL of 50 mM sodium acetate (pH 5.0), 1 mg/ml BSA, 0.01% Tween 20, and 12.5% glycerol without enzyme. Compound 23 was active at <1 millimolar concentration.

What is claimed is:

1. A compound of formula

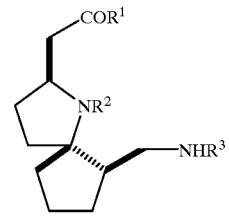

wherein R$^1$ is hydroxy, lower alkoxy, benzyloxy, NR$^4$R$^5$ or a solid
   substrate;
   R$^2$ is hydrogen, a first amino-protecting group, or an oligomer radical;
   R$^3$ is hydrogen, a second amino-protecting group or an oligomer radical;
   R$^4$ is hydrogen, alkyl, aryl, heterocyclyl, arylalkyl or heterocyclylalkyl; and
   R$^5$ is hydrogen, alkyl, aryl, heterocyclyl, arylalkyl or heterocyclylalkyl or a solid substrate.

2. A compound according to claim 1 wherein $R^1$ is hydroxy.

3. A compound according to claim 2 wherein $R^2$ is a first amino-protecting group and $R^3$ is a second amino-protecting group.

4. A compound according to claim 2 wherein one of $R^2$ and $R^3$ is hydrogen and the other is chosen from t-butoxycarbonyl, allyloxycarbonyl, benzyloxycarbonyl, and fluorenylmethoxycarbonyl.

5. A compound according to claim 2 wherein one of $R^2$ and $R^3$ is t-butoxycarbonyl and the other is chosen from allyloxycarbonyl, benzyloxycarbonyl, and fluorenylmethoxycarbonyl.

6. A compound according to claim 1 wherein one of $R^2$ and $R^3$ is hydrogen and the other is an amino-protecting group.

7. A compound according to claim 6 wherein one of $R^2$ and $R^3$ is hydrogen and the other is chosen from t-butoxycarbonyl, allyloxycarbonyl, benzyloxycarbonyl, and fluorenylmethoxycarbonyl.

8. A compound according to claim 1 wherein $R^1$ is —$NR^4R^5$ or a solid substrate and $R^2$ and $R^3$ are oligomer radicals.

9. A compound according to claim 1 wherein $R^1$ is —$NR^4R^5$ or a solid substrate, $R^2$ is a first amino-protecting group, $R^3$ is a second amino-protecting group and $R^5$ is a solid substrate.

10. A compound according to claim 1 wherein $R^1$ is —$NR^4R^5$ or a solid substrate, $R^5$ is a solid substrate, one of $R^2$ and $R^3$ is hydrogen and the other is chosen from t-butoxycarbonyl, allyloxycarbonyl, benzyloxycarbonyl, and fluorenylmethoxycarbonyl.

11. A compound according to claim 9 wherein one of $R^2$ and $R^3$ is t-butoxycarbonyl and the other is chosen from allyloxycarbonyl, benzyloxycarbonyl, and fluorenylmethoxycarbonyl.

12. A compound according to claim 1 wherein $R^1$ is lower alkoxy, one of $R^2$ and $R^3$ is hydrogen and the other is chosen from t-butoxycarbonyl, allyloxycarbonyl, benzyloxycarbonyl, and fluorenylmethoxycarbonyl.

* * * * *